US009675291B2

(12) United States Patent
Braspenning et al.

(10) Patent No.: US 9,675,291 B2
(45) Date of Patent: Jun. 13, 2017

(54) MODIFYING A PSYCHOPHYSIOLOGICAL STATE OF A SUBJECT

(75) Inventors: Ralph Braspenning, Eindhoven (NL); Mark Thomas Johnson, Eindhoven (NL); Ronaldus Maria Aarts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 562 days.

(21) Appl. No.: 12/920,879

(22) PCT Filed: Mar. 6, 2009

(86) PCT No.: PCT/IB2009/050943
§ 371 (c)(1),
(2), (4) Date: Sep. 3, 2010

(87) PCT Pub. No.: WO2009/112990
PCT Pub. Date: Sep. 17, 2009

(65) Prior Publication Data
US 2011/0004047 A1 Jan. 6, 2011

(30) Foreign Application Priority Data
Mar. 14, 2008 (EP) .................................... 08152732

(51) Int. Cl.
*A61B 5/16* (2006.01)
*A61B 5/024* (2006.01)
*A61B 5/0452* (2006.01)

(52) U.S. Cl.
CPC ............ *A61B 5/16* (2013.01); *A61B 5/02405* (2013.01); *A61B 5/0452* (2013.01); *A61B 5/165* (2013.01)

(58) Field of Classification Search
CPC ... A61B 5/0006; A61B 5/02405; A61B 5/165; A61B 5/16; A61B 5/0452; A61B 5/7235;
(Continued)

(56) References Cited

U.S. PATENT DOCUMENTS 3,278,676 A * 10/1966 Becker .......................... 348/484
4,632,126 A 12/1986 Aguilar
(Continued)

FOREIGN PATENT DOCUMENTS

| CN | 1912862 A | 2/2007 | |
| EP | 1551178 A1 * | 7/2005 | ............... H04N 5/64 |

(Continued)

OTHER PUBLICATIONS

Resperate | Lower Blood Pressure Naturally—webpage http://www.resperate.com/, Accessed online on Dec. 5, 2016.
(Continued)

*Primary Examiner* — Christine H Matthews
*Assistant Examiner* — Kaylee Wilson
(74) *Attorney, Agent, or Firm* — Sherry Womack Austin

(57) ABSTRACT

An apparatus and method for modifying a psychophysiological state of a subject include detecting a psychophysiological measure of the subject; processing the detected physiological measure so as to provide a signal indicative of a psychophysiological state of the subject; and outputting at least one of an audio stimulus, visual stimulus, haptic stimulus, temperature stimulus and scent stimulus to the subject. The output stimulus may be derived from an audio-visual data signal provided to the apparatus. Further, the output stimulus is adjusting in real time based on the signal indicative of a psychophysiological state of the subject.

23 Claims, 9 Drawing Sheets

(58) Field of Classification Search
CPC ... A61B 5/7239; A61B 5/7242; A61B 5/7246; A61B 5/7282; A61N 1/3702
USPC .......................... 600/509, 2–286; 607/1, 80
See application file for complete search history.

(56) References Cited

U.S. PATENT DOCUMENTS

| | | | |
|---|---|---|---|
| 4,882,535 | A | 11/1989 | Gavish |
| 4,987,901 | A * | 1/1991 | Kunig ............................ 600/509 |
| 5,076,281 | A | 12/1991 | Gavish |
| 5,253,168 | A | 10/1993 | Berg |
| 5,343,871 | A * | 9/1994 | Bittman ............... A61B 5/0482 128/905 |
| 5,423,328 | A | 6/1995 | Gavish |
| 5,720,619 | A | 2/1998 | Fisslinger |
| 5,749,367 | A * | 5/1998 | Gamlyn et al. ............... 600/509 |
| 5,800,337 | A | 9/1998 | Gavish |
| 5,997,482 | A * | 12/1999 | Vaschillo et al. ............. 600/484 |
| 6,026,322 | A * | 2/2000 | Korenman ........... A61B 5/0017 600/547 |
| 6,090,037 | A | 7/2000 | Gavish |
| 6,305,943 | B1 | 10/2001 | Pougatchev |
| 6,358,201 | B1 | 3/2002 | Childre |
| 6,527,700 | B1 | 3/2003 | Manico et al. |
| 6,656,137 | B1 * | 12/2003 | Tyldsley et al. ............... 601/15 |
| 6,662,032 | B1 | 12/2003 | Gavish |
| 6,806,911 | B2 * | 10/2004 | Takemoto ..................... 348/554 |
| 7,117,032 | B2 | 10/2006 | Childre |
| 7,163,512 | B1 | 1/2007 | Childre |
| 8,260,405 | B2 | 9/2012 | Aarts |
| 2003/0009078 | A1 * | 1/2003 | Fedorovskaya et al. ....... 600/26 |
| 2003/0063222 | A1 * | 4/2003 | Creed et al. .................. 348/687 |
| 2003/0100924 | A1 | 5/2003 | Foreman |
| 2003/0131351 | A1 | 7/2003 | Shapira |
| 2003/0144572 | A1 | 7/2003 | Oschman |
| 2004/0077934 | A1 | 4/2004 | Massad |
| 2004/0116784 | A1 | 6/2004 | Gavish |
| 2005/0033189 | A1 | 2/2005 | McCraty |
| 2005/0124906 | A1 | 6/2005 | Childre |
| 2005/0209504 | A1 * | 9/2005 | Elliott ............................. 600/26 |
| 2005/0288601 | A1 * | 12/2005 | Wood et al. ................... 600/513 |
| 2006/0058590 | A1 | 3/2006 | Shaw |
| 2006/0102171 | A1 | 5/2006 | Gavish |
| 2006/0111745 | A1 | 5/2006 | Foreman |
| 2006/0111746 | A1 | 5/2006 | Foreman |
| 2006/0142968 | A1 * | 6/2006 | Han et al. ..................... 702/120 |
| 2007/0021675 | A1 | 1/2007 | Childre |
| 2007/0066916 | A1 | 3/2007 | Lemos |
| 2007/0106183 | A1 * | 5/2007 | Suzuki et al. ................. 600/595 |
| 2008/0001735 | A1 * | 1/2008 | Tran ........................ 340/539.22 |
| 2010/0113950 | A1 * | 5/2010 | Lin et al. ...................... 600/509 |
| 2010/0240945 | A1 * | 9/2010 | Bikko ............................. 600/28 |

FOREIGN PATENT DOCUMENTS

| | | |
|---|---|---|
| JP | 05345028 | 12/1993 |
| JP | 2004222818 A | 8/2004 |
| JP | 2006246437 A | 9/2006 |
| JP | 2007535215 A | 11/2007 |
| WO | 0189368 A2 | 11/2001 |
| WO | WO 0189368 A2 * | 11/2001 |
| WO | 2005020575 A1 | 3/2005 |
| WO | 2005044092 A2 | 5/2005 |
| WO | 2007091199 A2 | 8/2007 |

OTHER PUBLICATIONS

Patterson, R.B. et al., "Voluntary Cardio-Respiratory Synchronization", IEEE Engineering in Medicine and Biology Magazine, 23(6), pp. 52-56, Nov./Dec. 2004.

Harland, C.J. et al., "High Resolution Ambulatory Electrocardiographic Monitoring using Wrist-Mounted Electric Potential Sensors", Institute of Physics Publishing, Measurement Science and Technology, 14 (2003), pp. 923-928.

Brink M. et al., "Contact-Free Measurement of Heart Rate, Respiration Rate, and Body Movements During Sleep", Behavior Research Methods, 38(3), pp. 511-521, 2006.

Morbiducci, U. et al., "Optical Vibrocardiography: A Novel Tool for the Optical Monitoring of Cardiac Activity", Annals of Biomedical Engineering, vol. 35(1), pp. 45-58, Jan. 2007.

Nilsson, L. et al., "Respiratory Monitoring using Reflection Mode Photoplethysmography", PhD Thesis NR. 898 Linkopings University 2005, ACTA Anaesthesiologica Scandinavica, 2007, 51: 130.

Han, K et al., "Decomposition of Heart Rate Variability by Adaptive Filtering for Estimation of Cardiac Vagal Tone", Proceedings of the Annual International Conference of the IEEE Engineering in Medicine and Biology Society, Orlando, FL, U.S., Oct. 31-Nov. 3, 1991, New York, IEEE, US, vol. 13, No. 2 (Oct. 31, 1991), pp. 660-661.

Sshin, Shaw-Jyh et al., "Assessment of Autonomic Regulation of Heart Rate Variability by the Method of Complex Demodulation," IEEE Transactions on Biomedical Engineering, New York, NY, U.S., vol. 36, No. 2 (Feb. 1989), XP000009587, pp. 274-283.

Zhao, L. et al., "Derivation of Respiration from Electrocardiogram During Heart Rate Variability Studies", Computers in Cardiology (1994), pp. 53-56, XP-002322495.

Task Force of the European Society of Cardiology and the North American Society of Packing and Electrophysiology, Special Report, "Heart Rate Variability: Standards of Measurement, Physiological Interpretation and Clinical Use", pp. 1043-1065, XP002236874, European Heart Journal, vol. 17, Mar. 1996, pp. 354-381.

Berntson, G.G. et al., Committee Report, "Heart Rate Variability: Origins, Methods, and Interpretive Caveats", Psychophysiology, Cambridge University Press, U.S.A., vol. 34 (1997), pp. 623-648, XP009045636.

Junnila, S. et al, "An EMFi-Film Sensor Based Ballistocardiographic Chair Performance and Cycle Extraction Method", IEEE Workshop on Signal Processing Systems Design and Implementation, 2005. vol. Issue 2-4, pp. 373-377, Nov. 2005.

Cysarz, D et al., "Cardiorespiratory Synchronization during Zen Meditation", European Journal of Applied Physiology, 95(1): pp. 88-95, 2005.

Jovanos, E. et al., "On Spectral Analysis of Heart Rate Variability during Very Slow Yogic Breathing", 27th Annual International Conference of the Engineering in Medicine and Biology Society, IEEE-EMBS 2005. pp. 2467-2470, 2005.

Heartmath webpage, http://www.heartmath.com, Accessed online on Dec. 5, 2016.

Wilddivine Wild Divine: Biofeedback Meditation, Mindfulness and Mind/Body Training-webpage, http://www.wilddivine.com, Accessed online on Dec. 5, 2016.

Bogert, B.P. et al, "The Quefrency Alanysis of Time Series for Echoes: Ceptstrum, Pseudo-Autocovariance, Cross-cepstrum and Saphe Cracking", in Proceedings of the Symposium on Time Series Analysis (1963), pp. 209-243.

Ekman, R "Question 6: Is There Emotion Specific Physiology?", The Nature of Emotion, Fundamental Questions, Series in Affective Science, Dec. 1994, pp. 235-262 http://www.amazon.co.uk/Nature-Emotion-Fundamental-Questions-Affective/dp/0195089448#reader_0195089448.

* cited by examiner

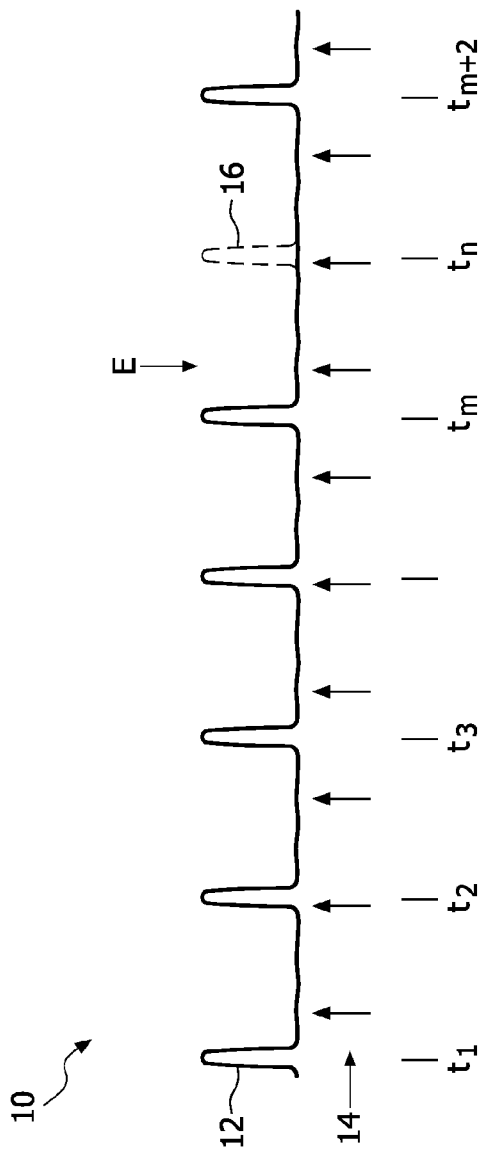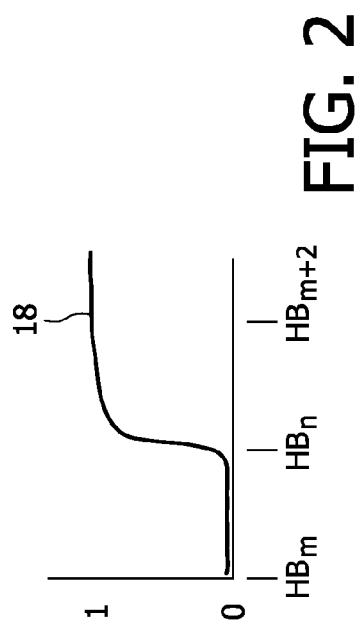

MODIFYING A PSYCHOPHYSIOLOGICAL STATE OF A SUBJECT

FIELD OF THE INVENTION

This invention relates to modifying a psychophysiological state of a subject and more particularly to modifying a psychophysiological state of a subject based on a physiological measure of the subject.

BACKGROUND OF THE INVENTION

Helping people to attain a desired psychophysiological state is an important and large business area since people generally aspire and seek to reach a happy and/or relaxed state as often as may be possible. Particular importance is often placed upon relaxation and attaining a relaxed state of body and mind. Thus many relaxation products and services are available which are directed to helping a user relax, for example books, saunas, music theatre, etc.

Typically such products and services are passive in that they do not take into account the psychophysiological state. Accordingly they do not efficiently influence a user's psychophysiological state and can therefore consume a large amount of a user's time.

It is desirable to develop a way of assisting a person in the process of reaching a desired psychophysiological state so as to reduce the possibility of wasting valuable time and/or money that may otherwise be spent attempting reach such a state.

It is known that systems can be used to measure psychophysiological-related data from human beings. Further systems have been proposed which are adapted to actively monitor biometric data (such as heart rate variability or skin conductance levels) of a user and to stimulate the user based on the detected biometric data in an attempt to reach a relaxed state. Typically in such systems a game or challenge is presented to the user to encourage the user to lower stress levels and become more relaxed.

United States Patent Application Publication Number US 2006/0142968 A1 discloses a home control system using galvanic skin responses and heart rate information.

SUMMARY OF THE INVENTION

A current value of the output stimulus may be manipulated so as to derive a new value of the output stimulus, wherein the new value is based on the signal indicative of a psychophysiological state of the subject and the current value of the output stimulus. The invention may therefore enable a user to relax through adaptation of a stimulus seen, heard, felt, or scented by the user and derived from an audio-visual (A/V) data stream/signal.

An A/V signal will be understood to be an analogue or digital audio/video signal provided from an A/V source, the A/V signal typically being transmitted over an A/V cable or communication link to an A/V receiver for output/display on equipment and/or applications that deal with sound and sight. Exemplary A/V sources include CDs, DVDs, celluloid film, television broadcasts, solid state memory devices such as flash memory and other sources which are adapted to store or provide A/V content. A/V content can include music, speech and/or video. A/V content may for example be provided by a MP3 player that is coupled via a USB port to the apparatus. The apparatus according the invention may comprise a TV for providing the visual stimulus. Said TV may comprise a tuner for receiving the television broadcast and a DVD player or a hard disk or other solid state memory device for storing A/V content.

Thus, the stimulus can be audible/visible media content from a recorded source or live broadcast. This content may be movie and/or music from a DVD or a broadcast or another A/V source selected by the user. Such a relaxation process may appear different every time thereby preventing the relaxation process from becoming a boring repeated exercise. In another example, the apparatus comprises a TV with ambient lighting means the visual stimulus comprising the light provided by the ambient lighting means and said light being for example dependent on the dominant color of the selected visible media content (e.g. a DVD, a broadcast, or another A/V source selected by the user).

Thus the invention may help a person to reach a relaxed psychophysiological state for example by actively assessing psychophysiological or biometric data and manipulating an audio/visual/haptic/temperature/scent stimulus presented to the person. In particular embodiments of the invention detect and monitor biometric signals of a person to determine a psychophysiological state of the person. Information about the determined state can then be used to manipulate a stimulus (such as for example a video displayed on a display screen or the color and intensity of lighting, vibration of a remote control located in a hand of the user) visible/audible/tangible to the user so as to influence their breathing cycle and psychophysiological state.

Embodiments of the invention may therefore be used in conjunction with multimedia equipment to enhance a user's experience and help them relax. Such embodiments may be adapted to encourage a user to breathe in synchronization with a stimulus output by the multimedia equipment. For example the visual appearance of a television display may be periodically changed providing a visual stimulus to initiate the relaxation while the visual stimulus further comprises for example light provided by ambient lighting means that are included in the television. The intensity and/or color of the light is modified in response to the determined psychophysiological state of the user thereby rewarding the user for becoming relaxed. In a further example an audio/visual output stimulus is provided by a CD (compact disk) radio alarm clock that further comprises a light source. The audio/visual output stimulus comprises preferably a periodically changing sound to initiate the relaxation. The audio/visual stimulus further comprises the lighting provided by the light source. The intensity of the light source may be dimmed as the user is getting more relaxed and this may assist the user in falling asleep.

The stimulus used to influence a user's breathing cycle may be developed as a separate, dedicated mode of operation of a television. Alternatively such a stimulus may be superimposed on or around the normal mode of a television or display unit. By way of example a television image could cyclically alternate in intensity or lighting in the vicinity of the television display could vary in intensity (independently of the television image content) whilst the television image is undistorted.

BRIEF DESCRIPTION OF THE DRAWINGS

Embodiments of the invention will now be described, purely by way of example, with reference to the accompanying drawings, in which:

FIG. 1 illustrates an ECG waveform used to explain principles of the present invention;

FIG. 2 illustrates an event detection probability curve for the event timing of FIG. 1;

FIG. 10 is a graph illustrating an exemplary progression of a user's change in psychophysiological state over time when using the apparatus of FIG. 9a.

The dimensions of the diagrams are not to scale and like reference numerals refer to like elements throughout.

DETAILED DESCRIPTION OF THE EMBODIMENTS

Figure 3:
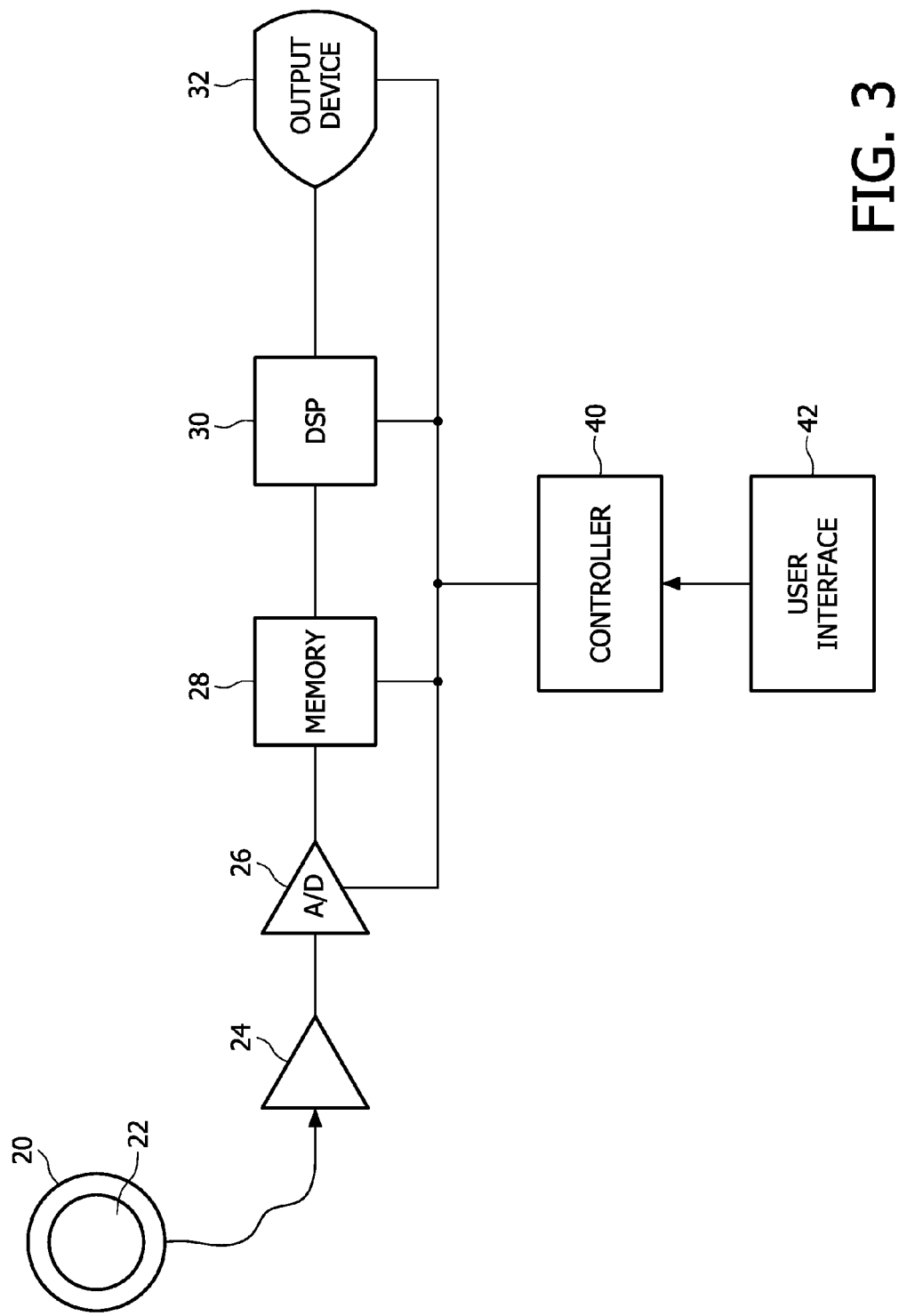
FIG. 3 illustrates in block diagram form an psychophysiological state detection device constructed in accordance with the principles of the present invention.

The present invention provides a method and apparatus for assessing and modifying a psychophysiological state of a person thereby helping such a person (a user or subject) to reach a relaxed state for example. The present invention also provides a method and apparatus for assessing and modifying the psychophysiological states of two or more persons thereby helping these persons to reach a common relaxed state for example by attempting to achieve a coherence of their heart rate variability.

Embodiments of the invention provide a device and method for modifying a psychophysiological state of a person. The psychophysiological state of a person is determined based on psychophysiological measurements for example detected biometric signals. Based on the detected state, an audio/visual/haptic/temperature/scent stimulus presented to the person can be modified in real-time so as to influence a breathing and/or heart rate of the person. This process of detecting a psychophysiological state and modifying a stimulus in response to the detected state can be repeated periodically or continuously so as to modify/manipulate the state of the user towards a desired goal.

Referring first to FIG. 1 an ECG waveform of a subject (or user) being monitored is shown. It has been observed that when an individual is relaxed and directing his or her attention continuously on a given subject that individual's short-term heart rate remains steady or varies periodically. It has also been observed that when the individual's attention to the subject is interrupted by an external event or even the drifting of the individual's attention to a different subject there is a change in the short-term heart beat interval. It is hypothesized that these changes result from changes in the relative involvement of the sympathetic and the parasympathetic nervous systems on the heart.

The sympathetic nervous system is known to increase heart rate whereas the parasympathetic nervous system decreases heart rate. When an individual is stressed the individual's heart rate changes in response to variations in external events and brain activity with a lengthening or shortening of the heart beat interval and the heart can indeed actually skip a heart beat. Consequently it is observed that when an individual is stressed or rapidly changing their focus of attention that individual's short-term heart rate varies sporadically. These observations are applied in the invention to monitor and detect changes in a person's psychophysiological state.

FIG. 1 illustrates the application of these principles to detecting and/or monitoring the psychophysiological state of a subject. An ECG waveform 10 is seen to have R-waves 12 recurring at the regular intervals t1, t2, t3 . . . of a heart beat. The ECG waveform 10 is sampled as indicated by the sampling time arrows in row 14. As will be explained below these samples can be processed to deduce the regularity or irregularity of the heart beat. In this example the regular recurrence of the heart beat continues until an event transpires at the time of the event arrow E. This causes a disruption of the regular recurrence of the heart beat in this example a skipping of the next regularly expected R-wave 16 which should occur at time tn. The heart beat then resumes two heart cycles later with an R-wave at time tm+2. This missing heart beat cannot be detected following the R-wave occurring at time tm until a sample is obtained at or after the expected time tn of the occurrence of the next R-wave and the expected R-wave is found to be missing. The sample taken at the time of the sampling arrow at or just before time tn is the first time at which the missing R-wave 16 could be detected. As more and more samples are taken following the time tn the probability that the R-wave 16 will be detected as missing increases.

This probability is illustrated by the probability curve 18 in FIG. 2 where it is shown that there is virtually no possibility of detecting the R-wave missing at heart beat HBn following the heart beat HBm until the anticipated time of missing heart beat HBm or later. Following that time the probability that the absence of the expected heart beat will be detected rapidly increases, approaching near certainty by the time of the next actual heart beat HBm+2 at time tm+2 as the probability curve 18 indicates. It is therefore seen that the sampling of an ECG waveform can lead to the detection of a missing heart beat. The same technique can also lead to the detection of a heart beat which does not occur at the same regular interval as the preceding heart beats as described below. It is this understanding that underlies the following examples of the present invention in which change of psychophysiological state can be quickly detected in real time.

FIG. 3 illustrates a state detection device constructed in accordance with the principles of the present invention. The detection device is adapted to determine the regularity of the first heartbeat signal so as to provide an output signal indicative of a psychophysiological state of a person.

An electrode 20 is provided with a conductive layer 22 which receives a person's ECG signal. The electrode 20 is coupled to an amplifier 24 which amplifies the ECG signal which is then digitally sampled by an analog to digital converter 26. The digital samples of the ECG signal are stored in a memory 28. The ECG signal samples are coupled to a processor 30, in this example illustrated as a digital signal processor (DSP) which processes groups of samples by executing an algorithm which determines the short-term regularity of the heart cycle of the ECG signal as described more fully below. Based on the determined regularity of the heart cycle of the ECG, the processor 30 outputs an output signal containing parameters indicative of the psychophysiological state of the person.

The output signal indicative of detected psychophysiological state is coupled to an output device 32 which based on the parameters contained in the output signals modifies and outputs a visual and/or audible and/or tangible stimulus to the person so as to influence a breathing pattern of the person. For instance the output device could be a television 160 and the image displayed by the television could periodically alternate in intensity to indicate the times at which a person should inhale and/or exhale while the colors of the image displayed may be indicative of the psychophysiological state of said person. In this example the output stimulus comprises the displayed image, wherein the intensity of the image is periodically alternated for influencing the breathing pattern and the colors of the image are changed to indicate a change in the psychophysiological state of the person (e.g. the person is getting more relaxed). It will, however, be understood other output devices capable of outputting a stimulus to the user and modifying the stimulus in real-time based on the processor output may be used.

The active elements of the device are controlled by a controller 40 which can control variables affecting the process such as sampling time, algorithm processing variables, display parameters, output stimulus options, and the like. The controller 40 is in turn controlled by a user through a user interface 42 by which the user can control the process by determining time constants and/or other process variables.

Figure 4:
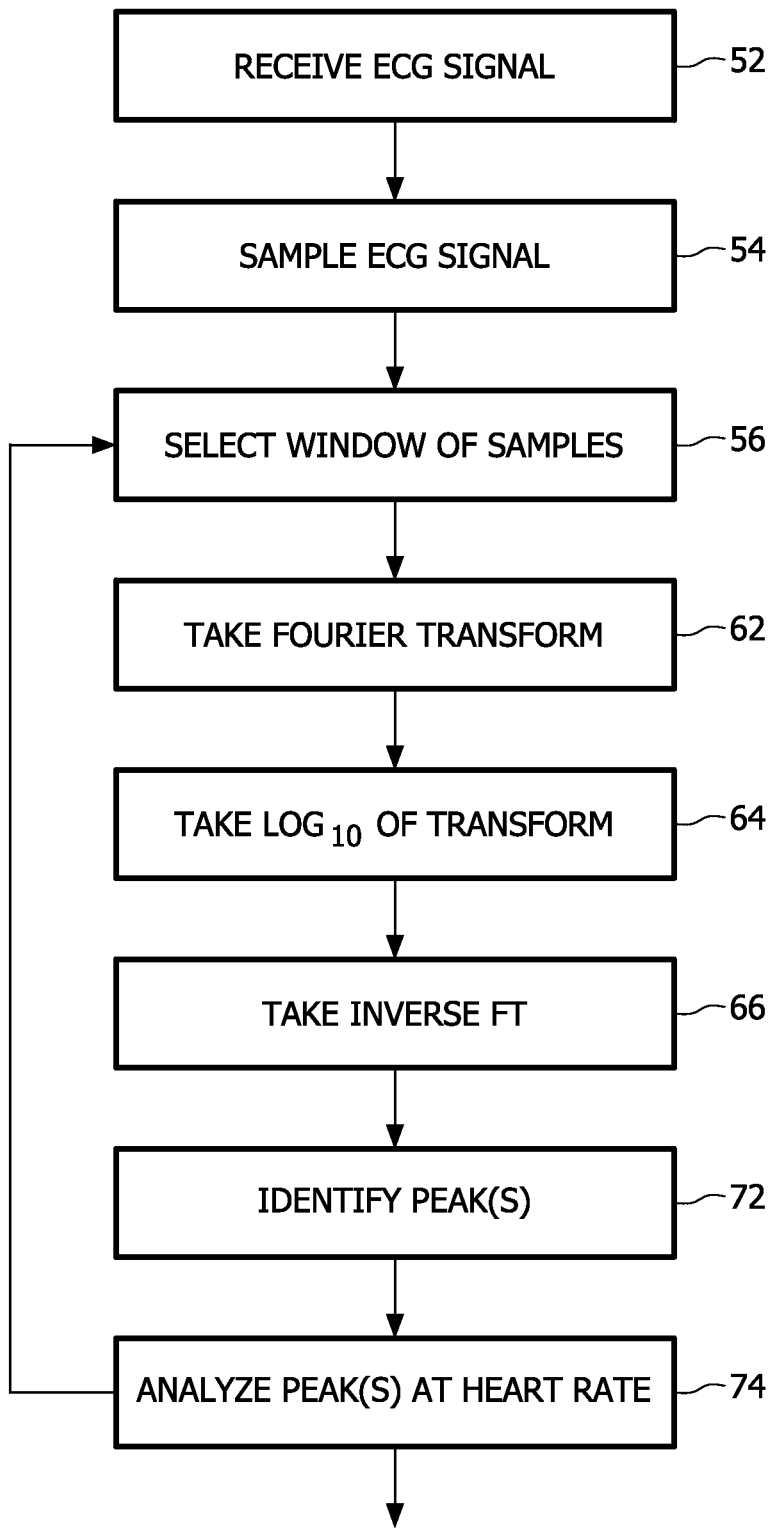
FIG. 4 is a flowchart of a method of monitoring changes in level of interest of a subject according to an embodiment of the invention.

FIG. 4 is an example of a method for monitoring changes in a psychophysiological state of a subject in accordance with the principles of the present invention. A subject's ECG signal is received in step 52 and sampled in step 54. From a sequence of signal samples a window or group of samples is selected for processing in step 56. Each group of samples is then processed to determine the regularity of the R to R interval which in a preferred embodiment is done by cepstrum processing.

Cepstrum analysis is a mathematical homomorphic transformation introduced in a 1963 paper by Bogert, Healy and Tukey. It is useful for determining periodicities in the autospectrum, the averaged magnitude of multiple instantaneous spectra. The cepstrum can be seen as providing information about the rate of change in different spectral bands. Cepstrum processing produces the inverse Fourier transform of the logarithm of the power spectrum of a signal. In signal processing the cepstrum is commonly viewed as the result of taking the Fourier transform of the decibel (logarithmic) spectrum as if it were a signal. Cepstrum processing has been applied in a variety of area including audio processing, speech processing, geophysics, radar, medical imaging, and others. In speech processing the cepstrum has been used to separate the words and pitch of a voice signal from the transfer function which contains the voice quality. In geophysics the cepstrum has been used to characterize the seismic echoes resulting from earthquakes and explosions. A device called the Heart Tuner which performs cepstrum analysis of an ECG waveform has been developed by Mr. Dan Winter to analyze and display a person's emotions. A person connected to the Heart Tuner watches the graphical displays produced and observes the harmonic content of his or her ECG waveform. As the person's emotions become positive the first cepstrum coherence peak is observed to rise. A person is taught to be empathetic by thinking shareable positive thoughts to increase the cepstrum coherence peak of the Heart Tuner. Cepstrum processing has also been used to analyze radar signal returns.

In the method of FIG. 4 cepstrum processing is used as illustrated in steps 62-66 to detect changes in the periodicity of the heart cycle as indicated by the R- to R-wave spacing. While the same information could be obtained by peak detection of the R-waves and measurement and comparison of the R-wave spacings, cepstrum processing is used in the illustrated method because of its robustness, its ready adaptation to a sampled data signal and its sensitivity to subtle changes in heart rate.

In step 62 the Fourier transform is taken of the window of samples selected in step 56. A log 10 is taken of this result in step 64. In step 66 an inverse Fourier transform is taken of the log result. This produces a series of values on a time axis exhibiting peaks corresponding to recurrent intervals of the sampled ECG waveform over the sampling interval of the window of step 56. The plots of FIGS. 5 and 6 graphically illustrate the results of this cepstrum processing.

Figure 5A:
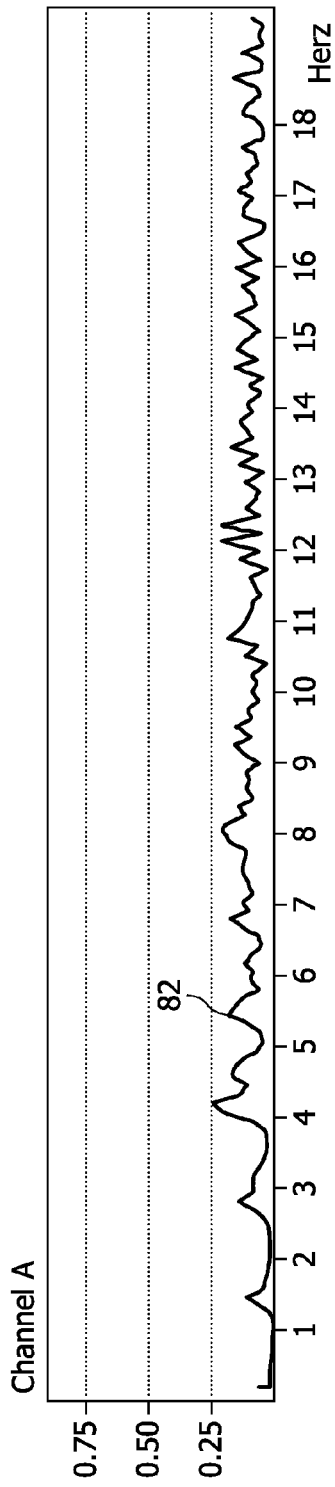
FIGS. 5a, 5b, 6a, and 6b are typical waveforms of an example of monitoring changes in a psychophysiological state of a subject in accordance with the principles of the present invention.
Figure 5B:
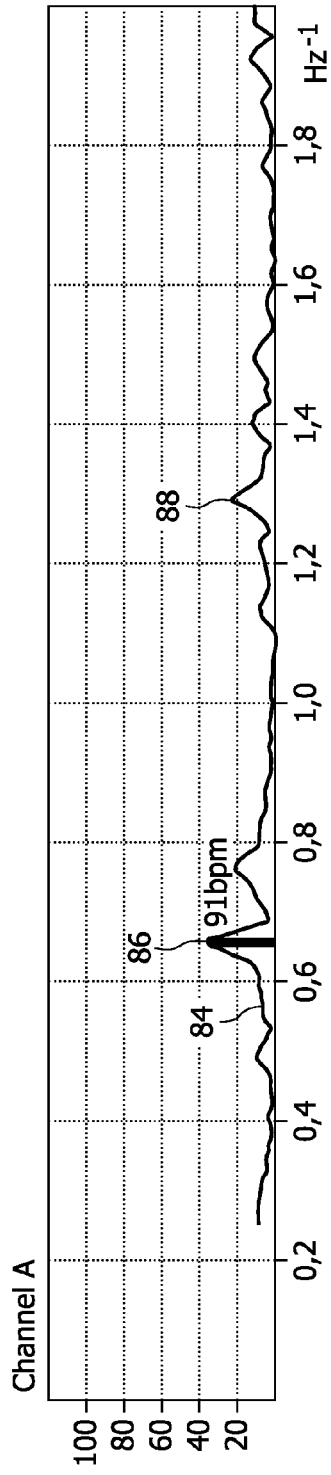

FIG. 5*a* illustrates the spectrum 82 of an ECG signal produced by taking a Fourier transform of the samples of the ECG waveform of a sequence of heart beats (step 62) in which the abscissa is in frequency (Hertz). In this example it is seen that the energy of the signal is distributed almost randomly over a wide range of frequencies. After a log 10 and an inverse Fourier transform are taken of this result (steps 64 and 66) by cepstrum processing, the result is a graph 84 on a time axis (Hertz-1, or seconds) as shown in FIG. 5*b*. The peaks of this graph 84 are identified in step 72 by any of a number of standard or sophisticated peak detection techniques.

In the example of FIG. 5*b*, several peaks may be observed, including those identified at 86 and 88. The dominant peak, also referred to hereinafter as the Cepstrum peak, for a heart rate is expected at the heart beat interval, such as the R- to R-wave interval. When analysis of these peaks 86 and 88 is performed to look for a heart rate interval (step 74), the peak 86 at 0.65 sec. is recognized as a heart beat of 91 beats per minute (bpm). The peak 88 at approximately 1.3 sec. is a subharmonic of the fundamental heart beat rate of 91 bpm. It is seen that in this example the amplitude of the Cepstrum peak 86 is relatively low. In accordance with the principles of the present invention a relatively low Cepstrum peak may indicate a low level of relaxation of the subject because the heart is not beating at a consistently constant rate. This result is communicated to the output device 32 in the device of FIG. 3 after cepstrum processing by the DSP 30 produces such a result.

Figure 6A:
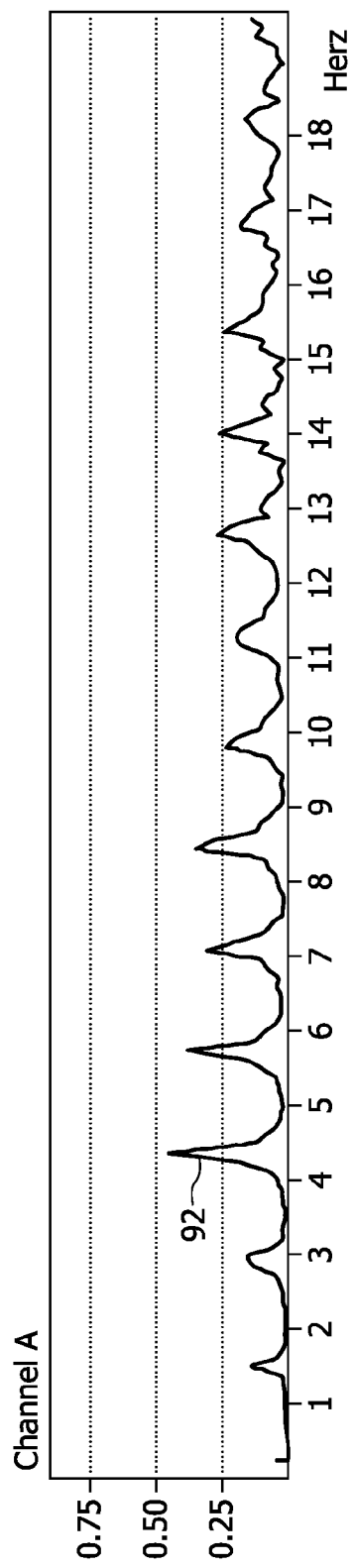
Figure 6B:
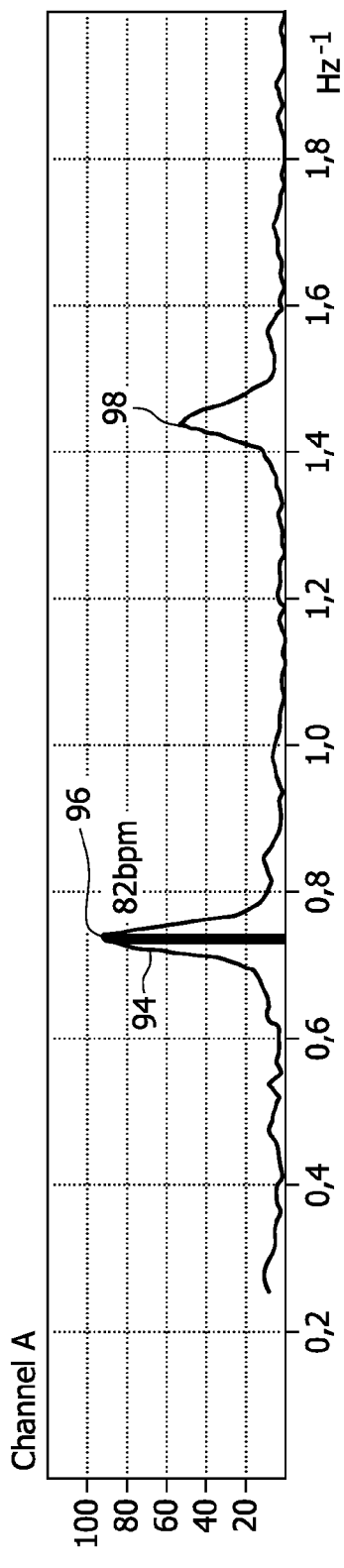

FIG. 6*a* illustrates a Fourier spectrum 92 of a different sequence of ECG signal samples. In this example the spectral energy is seen to coalesce around a series of well defined peaks. After a log 10 and inverse Fourier transform are taken of this data the time graph 94 of FIG. 6*b* results which is seen to exhibit two sharply defined peaks 96 and 98. The dominant peak at approximately 0.73 sec. is identified as the peak produced by a fundamental heart rate of 82 bpm and the peak 98 is a subharmonic peak at about 1.46 sec. The amplitude of the peak 96 is seen to be of a much higher magnitude than the corresponding peak of FIG. 5*b* indicating a very consistent heart rate.

This high magnitude peak 96 can be indicative of a high level of relaxation by the subject producing the ECG waveform of this data. The data of FIGS. 5 and 6 were taken from the same subject showing that at the time the window data for FIGS. 6a and 6b was acquired the subject was relaxed or focused on a specific subject and at the time the window data for FIGS. 5a and 5b was acquired the subject exhibited a lapse of attention or increased levels of agitation.

Figure 7:
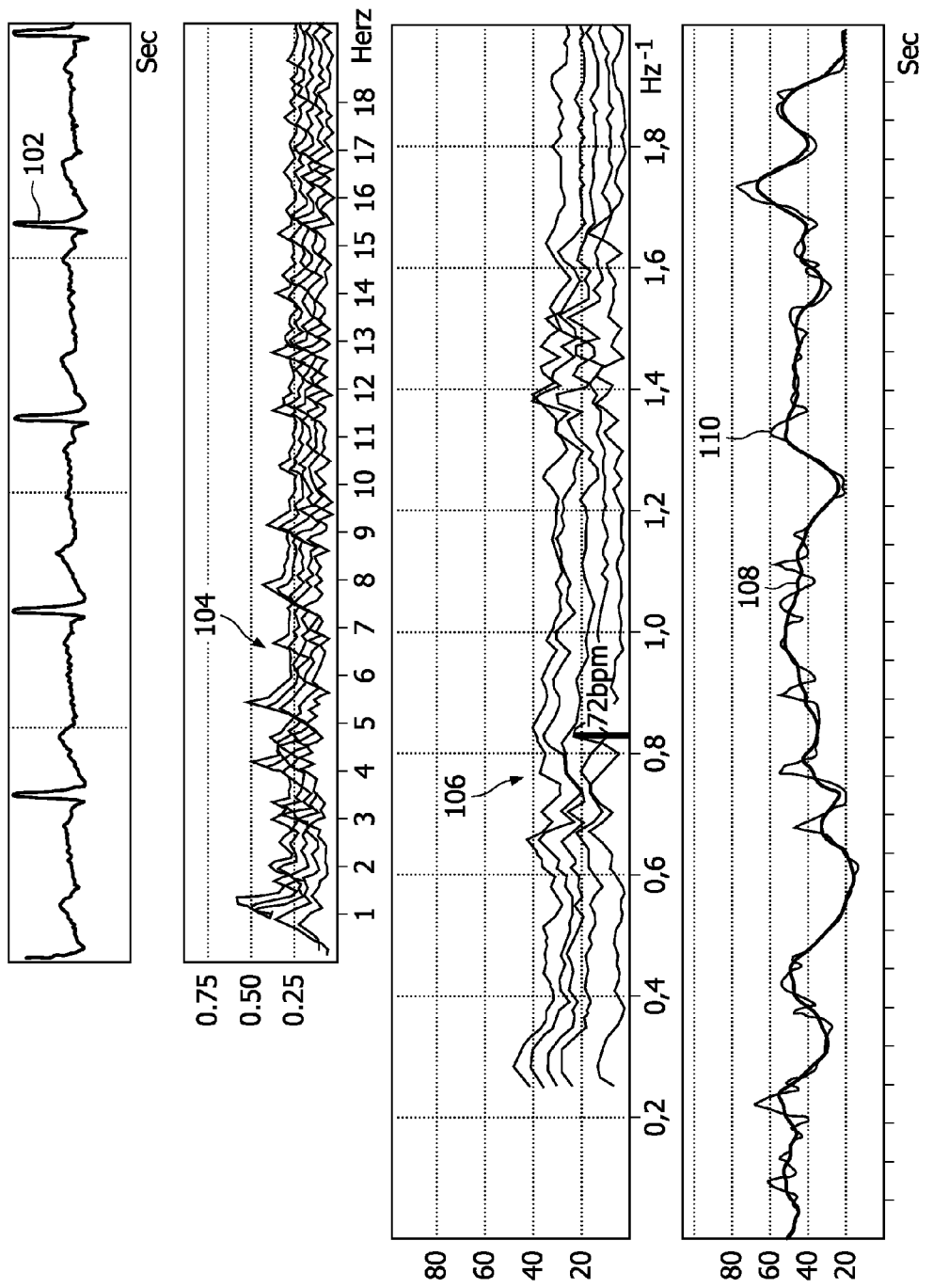
FIG. 7 illustrates typical waveforms for an example of monitoring changes in a psychophysiological state of a subject in accordance with the principles of the present invention.
Figure 8:
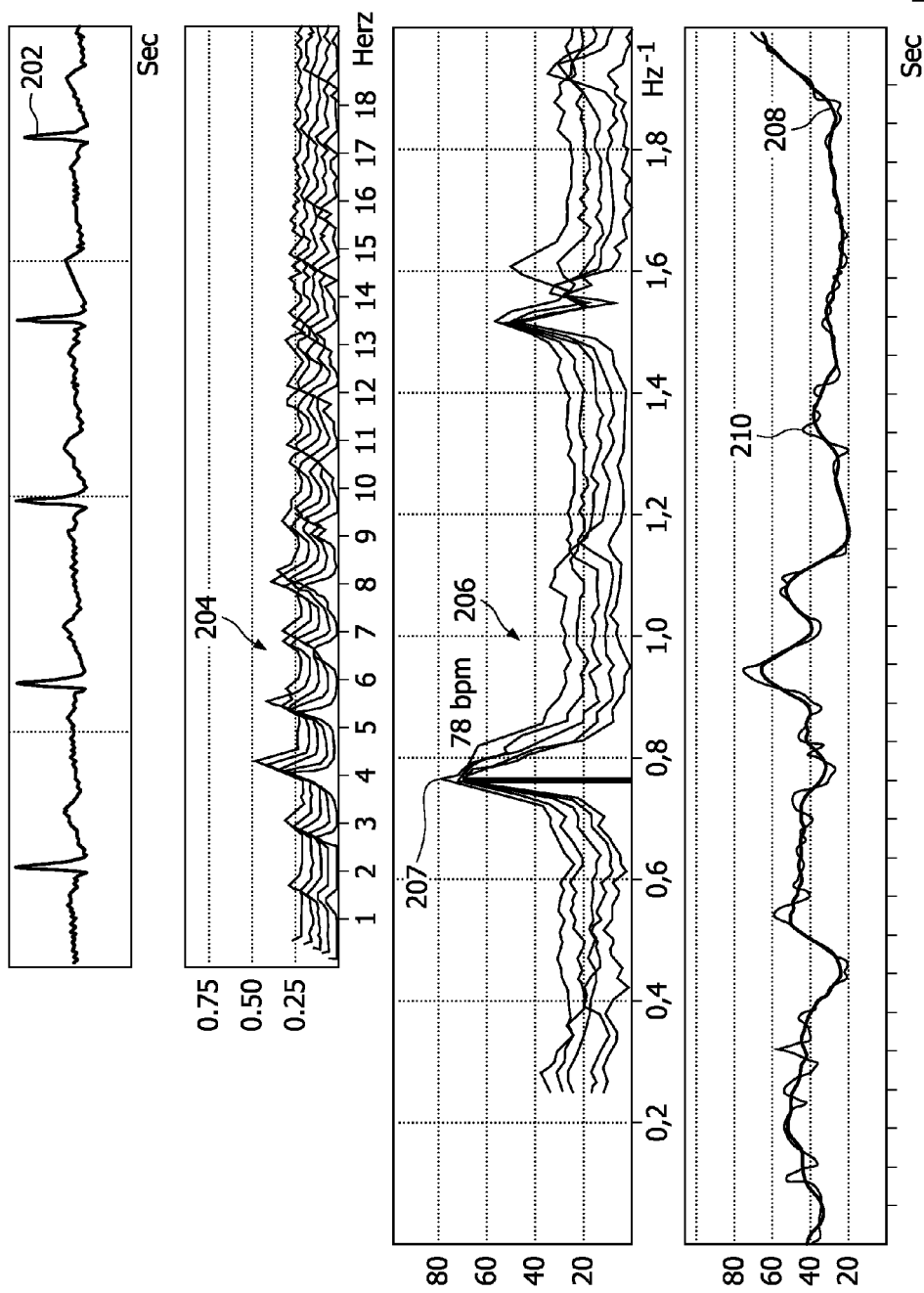
FIG. 8 illustrates typical waveforms for another example of monitoring changes in a psychophysiological state of a subject in accordance with the principles of the present invention.

In an embodiment of the present invention the short-term regularity of the heart rate is analyzed preferably by cepstrum processing to identify changes in a psychophysiological state of an individual. Examples of this are shown in FIGS. 7 and 8 in which trends in the fundamental cepstrum peak are analyzed to determine trends in the psychophysiological state of an individual. The rate-of-change of the cepstrum plot over time can be used as a criterion for a warning/indication of a change in psychophysiological state for example. The plot 102 at the top of FIG. 7 illustrates a subject's ECG waveform. In this example the ECG waveform is digitized (sampled) at a 500 Hz rate. After eight seconds of samples have been acquired a window of data is taken of these initial 4000 samples. This window of data then undergoes cepstrum processing as described above. This process is repeated by sliding the window every one-half second to take a different window of 4000 samples for cepstrum processing. The five graphs 104 in FIG. 7 illustrate the results of Fourier transform processing of five consecutive overlapping windows of 4000 samples. In this example the energy is seen to be fairly evenly distributed over the displayed spectrum. The five results of cepstrum processing of these data windows are shown at 106. These results are seen to exhibit a barely discernible peak at 72 bpm.

The cepstrum peaks of the five graphs 106 are averaged and plotted as a data point on the heavy line plot 108 at the bottom of FIG. 7. This plot is extended by a new cepstrum peak average calculated each time a new data window is cepstrum processed for a different set of five cepstrum peaks. Also plotted at a thin line 110 is a plot of the most recently calculated cepstrum peak. The plots of FIG. 7 are thus seen to show trends of the cepstrum processing with both a long and a short time constant. These lines 108 and 110 provide an indication of whether a subject's level of relaxation is increasing, decreasing, or staying constant.

FIG. 8 shows the results of the same processing of different data. The subject's ECG waveform 202 is seen to appear substantially the same as the ECG waveform 102 of FIG. 7. However the Fourier spectra 204 of the four most recent sample windows processed shows regularly recurring spectral peaks. The result of cepstrum processing of these spectra yield a series of high sharply defined fundamental cepstrum peaks 207 at 78 bpm in the cepstrum time plots 206. These high cepstrum peaks manifest themselves in the most recent trend lines 208 and 210 at the bottom of the drawing which are seen to strongly trend upward in the most recent time interval at the right side of the trend line plots.

Various data window sizes may be employed, such as windows ranging from 5 to 11 seconds and preferably in the range of 5.5 to 8 seconds. For persons with long attention spans longer windows may be desirable. Short-term heart beat regularity generally can be determined in eight to ten heart beats with the techniques described above. Sampling rates other than 500 Hz may be used. The output signal can be indicative of the magnitude of the instantaneous cepstrum peak or of the magnitude of the average of a plurality of cepstrum peaks or of the trend (increasing or decreasing) of the cepstrum signal. Various time constants can be used to produce the longer term averages. The cepstrum peak can be compared to a threshold level or a plurality of peak values can be integrated or differentiated to produce longer term indications of the level of concentration. Techniques other than cepstrum processing can be used such as analyzing the variance in a person's median heart rate.

As FIGS. 1 and 2 show changes in attention or a lapse in attention can be detected rapidly and in real time usually in two seconds or less.

Figure 9A:
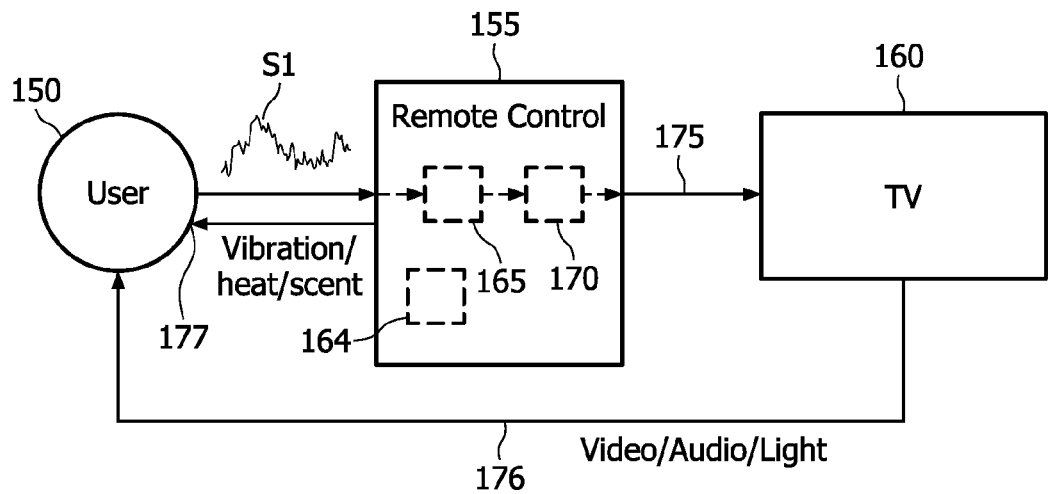
FIG. 9a shows an apparatus for modifying a psychophysiological state of a subject according to an embodiment of the invention.

Referring now to FIG. 9a, a system according to an embodiment of the invention is depicted. By detecting a biometric signal from the user the system modifies an audio/video/light stimulus output 176 to the user by the TV display apparatus based on a determined state of the user wherein the state of the user is determined based on the detected biometric signal.

FIG. 9a shows a user 150 of the system, the system comprising a remote control 155 and associated television display 160. Reference to a television display includes not only known rear projection or flat panel (LCD, LED, Plasma, or LASER) display but also projection apparatus adapted to project television signals. The remote control 155 may be similar to a conventional television remote control but further comprises: a heartbeat sensor 165 for detecting and monitoring a heartbeat signal S1 of the user 150; and a processor unit 170 for determining a psychophysiological state of the user based on an output from the heartbeat sensor 165.

In a further embodiment the remote control 155 further comprises storage means arranged to store data on heart rate variability of the user 150. This provides the advantage that the system may identify the user based on the stored data and select a preset of a parameter indicative of the user's psycho physiological state. Said preset may be dependent on said parameter obtained a previous time the system was used.

In yet a further embodiment the output unit further comprises a motive source 164 that may be situated in the remote control 155. The motive source may be selected from the group comprising motors, solenoids, piezo-electric devices, and shape-memory alloys. The remote control may for example further comprise a heating element or a cooling element (such as for example a Peltier element). As a further example the remote control may further comprise a reservoir the reservoir comprising a perfume. The remote control may release a scent relating to said perfume under control of the processor unit. The scent (such as for example lavender) may assist the user to relax. The output stimulus 176, 177 provided to the user may comprise at least one of the group comprising an audio, video, light, vibration, temperature, and scent stimulus.

Figure 9B:
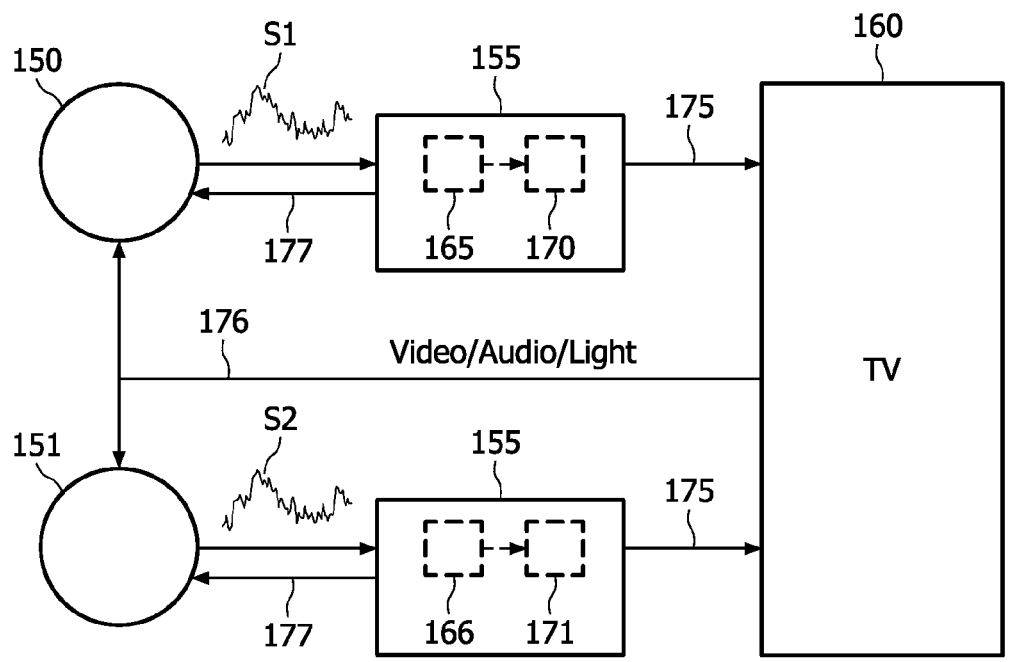
FIG. 9b shows an apparatus for modifying a psychophysiological state of a subject and a further subject according to an embodiment of the invention.

Referring now to FIG. 9b another system according an embodiment of the invention is depicted. By detecting biometric signals S1, S2 from the user 150 and the further user 151, the system modifies an audio/video/light/vibration/temperature/scent output stimulus 176, 177 provided by the TV display apparatus 160 and/or the remote control 155 to the user and the further user based on a determined psychophysiological state of the user and the further determined psychophysiological state of the further user. The state of the user and the further state of the further user are determined based on the detected biometric signals. For the detection of the biometric signals a heartbeat sensor 165 and a further heartbeat sensor 166 are used. Processor unit 170 and further processor unit 171 determine the psycho physiological state based on the output from heartbeat sensor 165 and heartbeat sensor 166.

In more detail referring to FIG. 9a, the user's heartbeat signal S1 is measured using any conventional heart rhythm (or electrocardiogram ECG) measurement sensor attached or connected to the remote control. It will be apparent to those skilled in the art that the heartbeat sensor 165 does not need to detect a complete ECG and that many alternative methods for detecting and/or monitoring a person's heart signal are known.

According to an embodiment of the invention the heartbeat sensor comprises a simple electrode integrated into the casing of the remote control 155 said electrode being suitable for detecting the pulse (i.e. the stroke output) of the user of the remote control 155. Alternatively the heartbeat sensor may comprise electrode(s) integrated into a bracelet or a belt such as the one used in the fitness and healthcare systems. The heartbeat sensor 165 may therefore be provided as a wired attachment to the remote control 155. It will also be appreciated that in alternative embodiments the heartbeat sensor 165 is adapted to monitor the complete heartbeat signal.

The processor unit 170 receives the data output of the heartbeat sensor 165 and processes the received data to determine a psychophysiological state of the user. In doing so the data is analyzed and reduced to a set of parameters indicative of the user's state. The set of parameters is then output by the processor unit 170 and communicated to the television display 160 via a suitable communication link 175. To this end the communication link 175 comprises a radio frequency RF link for example on the GSM and/or UMTS standard. It will however be understood that the other implementations of the communication link 175 are possible and based for example on Infra Red IR transmission, wired transmission, or wireless transmission.

The television 160 receives the set of parameters from the remote control 155 and based on the received set of parameters the television display adjusts its video and/or audio output by modulating its brightness and/or volume for example. The remote control may provide a haptic stimulus by providing a vibration pattern to the user. Via modulation of its output the television and/or the remote control can encourage the user to perform an activity such as inhalation/exhalation at one or more particular times thereby prompting the user to perform a pattern of activities. The pattern is designed to gradually relax the user through regular or repeated activity cycles that may gradually slow over time.

It is known that the breathing cycle of a person can be linked to their active emotional state. By prompting a person to inhale/exhale at predetermined times, the users can be encouraged to adapt their breathing cycle to a desired timing and pattern that is designed to be relaxing.

Figure 10:
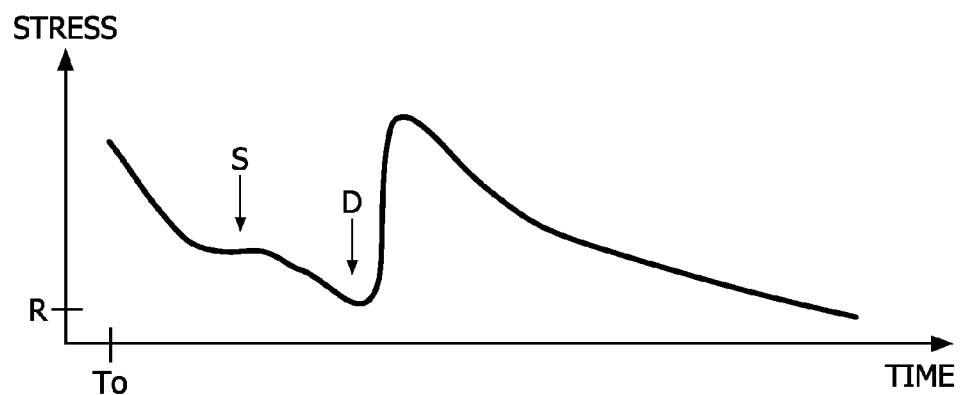

FIG. 10 illustrates an exemplary progression of a user's change in state over time. At the beginning (To) of the graph the user starts with a particular stress level and based on this detected level of stress the system outputs a stimulus which encourages the user to breathe in a cycle adapted to the detected level of stress. Gradually the system changes the cycle to decrease the stress level towards a desired value of stress R (which corresponds to the user being in a relaxed state) for example by increasing the length of time for each breathing cycle of the user.

At point S there is no further decrease in stress level over time but still the stress level is higher than the desired value R. The system then attempts to modify the breathing cycle of the user so as to further decrease the user's level of stress.

At point D a distraction occurs which startles the user and increases the user's stress level to high value. The system detects this resultant change in state and adapts the stimulus accordingly so as to restart the relaxation procedure from the new higher stress level. The system then repeats the process of modifying the output stimulus over time to gradually decrease the stress level of the user towards the desired value of stress R.

Figure 11:
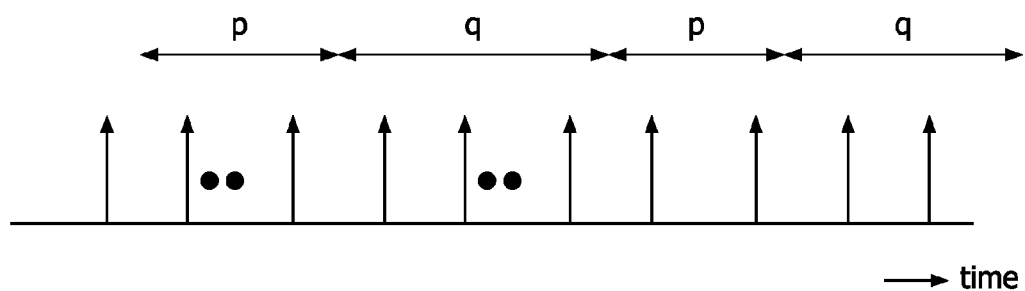
FIG. 11 is a timing diagram used to explain the principles of an embodiment of the invention.

Referring to FIG. 11 where arrows indicate a heartbeat and considering how the breathing cycle of a person may be manipulated by a stimulus one can assign intervals with real numbers p and q such that during the p interval or at the transition from q to p there is a 'breath in' control signal and at the transition from p to q there is a 'breath out' control signal. Between the p and q intervals there are int (p) and int (q) heartbeats respectively, where 'int' denotes the integer operation.

Note that p and q are not restricted to integers. These p and q may be chosen individually or even adapted to the subject, since this may depend on the subject's tidal volume and cardiac output.

The transients between p and q and vice versa are not necessarily coincident with a heart beat, p and q should simply vary proportional to the corresponding heart beat activity time axis so as to remain phase locked. In the simplest embodiment p and q are integers, and thus coinciding with the measured pulse (the arrows in FIG. 11).

In a preferred embodiment, the positions of the 'arrows' are predicted with an Auto Regressive (AR) filter so that in cases that the measured signal is unreliable the AR function predicts their correct position.

A preferred embodiment may also be adapted to determine initial values for p and q by letting the subject breath in and out in its own pace, and determining the breathing pace via an ECG-output. Typical values for p and q may be p=2, q=3, but as a starting value one can use initial values for p and q, and increase/decrease such numbers as required.

The heart beats need not be exactly in sync with the respiration but it suffices to be almost in sync. From the theory of weakly coupled chaotic systems it is known that if $|n\, \Phi_H - m\, \Phi_R| < \epsilon$, where n and m are integers, $\Phi_H$ and $\Phi_R$ are the phases of the heart and respiratory signals respectively and $\epsilon$ is a sufficiently small constant number the signals can be considered as being phase locked.

Heart Rate Variability (HRV) can also be detected by subtracting and averaging the interbeat interval, for example HRV at time i (HRV(i)) may be calculated using HRV(i)= $\alpha$*HRV(i−1)+(1−$\alpha$)*(t(i)−t(i−1)), where $\alpha$ determines the speed of the averaging process, and t(i) are the peaks in the PQRS complex (one heart beat's electric peak is called the "PQRS complex").

In alternative embodiments the television display 160 also comprises an ambient lighting arrangement (not illustrated) in its housing for adjusting the ambient lighting conditions within which the display 160 is situated. Thus instead of or in combination with adjusting the video and/or audio output the television 160 may modify the brightness or color of the ambient lighting arrangement based on the received set of parameters and independently of the video and/or audio output of the television 160.

In a further embodiment the invention provides a method and apparatus for assessing and modifying the psycho physiological state of two or more persons thereby helping these persons to reach a relaxed state for example. For each of said persons the psycho physiological state is determined based on psycho physiological measurements for example detected biometric signals. Based on the detected state the audio/visual/haptic/temperature/scent stimulus presented to each person is modified in real time so as to influence the breathing and/or heart rate of said person. For example the ambient lighting arrangement comprised in the television 160 may be split in parts each part providing a visual output for a person by modifying the brightness or color of said part of the ambient lighting arrangement based on the received set of parameters corresponding to said person. In a further embodiment the television 160 is arranged to provide a visual stimulus for each of said persons in a split-screen arrangement wherein each user receives a visual stimulus from a part of said split screen.

In yet a further embodiment said method and apparatus may be used to modify the psycho physiological state of two or more persons to a same state. This may for example be achieved by providing an audio/visual/haptic/temperature/scent stimulus to said persons to synchronize their heart rate variability. Each person may obtain its own stimulus, or there may be a common stimulus. For each of said persons the psycho physiological state is determined based on psycho physiological measurements, for example detected biometric signals. Based on the detected psycho physiological states the audio/visual/haptic/temperature/scent stimulus presented to said persons is modified in real time so as to influence their breathing and/or heart rate. For example a common audio/visual/haptic stimulus presented to said persons may be dependent on a difference in said detected psycho physiological states.

Regularity in a heart rate of a subject may be determined using Cepstrum processing, as explained earlier. The regularity in the heart rate may for example be a sinusoidal heart rate variation resulting in a peak in the Cepstrum graph referred to as Cepstrum peak. When for example two persons are breathing with a common stimulus the period of their heart rate variations will converge to the period of the common stimulus. Hence the heart rate variations of both persons will converge to each other, although the amplitude of the heart rate variation may differ for both persons for example one person may have a heart rate varying between 60 and 80 bpm while the heart rate of the other person varies between 70 and 90 bpm. In a further embodiment of the method and apparatus the Cepstrum peak of said persons is compared to determine a value of a coherence of their heart rate variability. That is when the Cepstrum peaks of both persons coincide they are breathing with a same period and hence both persons have a same heart rate variability. The common audio/visual stimulus may be further dependent on said value of the coherence.

It is noted that embodiments of the invention make use of the real-time processing possibilities of multimedia apparatus to process and manipulate an audio/visual signal (video, ambient light, audio . . . ) in response to a determined state of the user. In other words, a current value of the audio/visual signal can be modulated in response to the information indicative of the psychophysiological state of the user and the current value so as to derive a new value. This is different from a personal computer (PC) based approach where a computer program is only able to call upon a limited number of pre-defined responses (for example one of a list of possible animations within a computer game). In other words in a known PC-based approach a user has to follow pre-defined animations to become relaxed. Embodiments of the invention on the other hand enable a user to relax through real-time manipulation of a stimulus seen, heard, felt or scented by the user. By enabling the user to use any media content and not restricting the value of the output stimulus to a pre-defined set of responses the relaxation process can appear different every time. This prevents the relaxation process from becoming a boring repeated exercise as is the case for known PC-based approaches.

Today in most if not all living rooms a TV is present whereas a PC is more often located in the study. In many cases people enjoy to watch a movie provided by a DVD or broadcast while being in each other's company. Likewise it is attractive to relax with each other using the TV to provide a (for example common) audio/visual output stimulus to guide a relaxation exercise wherein the common output stimulus also shows the common progress of the relaxation.

The nature and amount of processing undertaken in the processor unit and the output device may vary between embodiments. For example the processor unit may undertake all of the required data processing and modification of the output stimulus so as to provide a signal that is simply output by the output device (which may therefore be a conventional output device). Alternatively the processor unit may simply relay signals from the sensor to the output device with the output device then processing the received signals and manipulating the output stimulus accordingly.

It should be noted that the above-mentioned embodiments illustrate rather than limit the invention, and that those skilled in the art will be capable of designing many alternative embodiments without departing from the scope of the invention as defined by the appended claims.

For example the heart rate signal can be acquired in many ways such as electrodes attached directly to a person's skin or in a person's clothing or seat or armrest. An ear clip or finger sensor could also be used to acquire the heart signal.

Also, psychophysiological measurements for determining a psychophysiological state of a subject can be obtained by detecting other biometric signals or data. For example information may be obtained by measuring pupil dilation and/or galvanic skin response. This can provide information regarding the emotional state (i.e. mood) of a subject. Facial expression interpretation obtained from video frame analysis can yield information on the valence of the emotional response (i.e. positive or negative). The method of Paul Ekman is suitable for this (see: 'The Nature of Emotions', by Paul Ekman, Richard J. Davidson).

Restlessness of persons is yet another parameter which is linked to the intensity of perceived emotions. Therefore, motion or posture analysis can provide additional information.

Embodiments of the invention may use real-time video processing to encourage a relaxation state of the user for example by persuading the user to breath slowly and regularly. For example the relaxation exercise could be superimposed upon the normal mode of a TV operation: for example the TV image could cyclically alternate in brightness or colorfulness, or an ambient lighting arrangement surrounding the housing of the TV could cyclically vary in intensity (independent from the displayed image content) whilst the TV image is undistorted.

Further embodiments may indicate the relaxation state of the user (and hence give the user feedback to how well they are relaxing). For example a complete image on a TV can be modified in real time according to the relaxation state of the user so that a more colorful image is displayed as the user gets more relaxed.

Of course a video output need not be modified. Instead an ambient lighting signal or audio output signal may be modified in real time according to the relaxation state of the user.

In a preferred embodiment one part of the system (either a half of the screen or the ambient-light intensity level or color etc.) provides a stimulus to the user whereas the other part of the system provides a stimulus that is modified in real time according to the relaxation state of the user. The user may then for example try to make the modified example as close to the original stimulus by becoming more relaxed.

From the embodiments described above it will be understood that the output stimulus provided to a user may be of any suitable form so as to influence a psychophysiological state of the user by indicating when the user should breathe for example. Purely by way of example a list of stimulus processing options will now be provided.

Colours and False Colors

An output image may be manipulated by changing the "color depth" of the image. For example the image may be changed from color to monochrome by either combining or ignoring some of the image color data. The user can recover the color content by increasing their measured degree of relaxation as measured by the physiological sensor(s). In other words the user may receive a reward (in this case a more colorful picture) for becoming more relaxed. In other examples, the output display device may make the colors of a video image even more vibrant than in real life, the user then receiving a reward of a "psychedelic" image for becoming relaxed.

Brightness and Contrast

An output image can be manipulated by changing either the maximum brightness of the image and/or its contrast (the ratio between the maximum and minimum brightness levels) by for example changing some of the video data in real time. The user can make the image more "sparkling" (i.e. brighter, sharper and more contrast) than the original image by increasing their measured degree of relaxation.

Audio Channel Manipulation

Output content may be manipulated by changing an audio channel. In an example the audio may be changed from its natural sound frequency to an un-natural frequency by adjusting the pitch of the audio data. The user can recover the natural content by increasing their measured degree of relaxation. In other words the user receives a reward (more natural sound) for becoming more relaxed. Alternatively the user may find it amusing to hear the distorted sound track, in which case the distorted sound may be provided as being a "reward" for their relaxation. In other examples the TV may introduce "surround sound" effects (by artificially changing the phase of the audio signal) to give the impression of a far "fuller" sound.

3D Depth Effects

Introduction of 3D effect is a highly desired feature amongst users of multimedia equipment. As a result many manufacturers are producing 3D display systems. Systems where a television display is provided with lenticular lenses (which direct 2 or more images in directions towards the left and right eyes of the viewers) or provided with glasses (which prevent one of the two stereo images from reaching one of the viewer's eyes) have been proposed. For relaxation purposes it may be preferred to use the lenticular approach (as the user may consider the glasses to be somewhat intrusive and may interfere with the desired relaxation effect). Within such embodiments, the image may be manipulated by changing the "3D depth" of a displayed image i.e. how far the image is perceived by the viewer to emerge from the screen. By way of example the image may be changed from standard 2D to 3D with limited depth to "full 3D" by real time manipulation of the video data directed to the left and right eye of the user. The user can increase the 3D perception by increasing their measured degree of relaxation as measured by the physiological sensor(s).

Shape/Aspect Ratio

An output image may be manipulated by changing the width and/or height of the image as is often done on conventional wide screen televisions for displaying normal video content. In an example a displayed image may be changed from a first shape/size to a second less distorted shape/size by real time manipulation of the video data. The user can change the shape/size of the displayed image by increasing their measured degree of relaxation.

Image Distortions

Image distortions are somewhat similar to adjusting the aspect ratio, but differ in that the image is distorted by more than just changing its width and height (i.e. there are also some non-linear distortions). Examples of such distortions may be the magnification of a portion of the image the addition of a slanted distortion, or "wavy" distortion over the picture). Another example may be to start with the impression that the image is at the end of a long tunnel whilst the image gets "closer" as the user relaxes.

Ambilight and Ergolight

"Ambilight" (a light provided in the frame of the television so as to modify the ambient lighting conditions around or in the vicinity of the television) and "Ergolight" (a similar concept but providing multi-colored lighting on the viewer's side of the television frame) have been proposed and are provided in the housing of some conventional televisions. Such ambient illuminating means are designed to change in response to audio and/or video data (for example, an AV signal) of the television so as to enhance the viewing conditions or experience of the viewer. Embodiments may employ such ambient lighting means to provide the visual stimulus which is modified in response to the determined psychophysiological state of the user. In doing so, the ambient lighting means can be used not only to initiate the relaxation but also to reward the user for becoming relaxed by becoming extra bright or colorful.

Time, Speed

The playing speed of video material may be varied. For instance the speed of playback can be linked to the state relaxation of the user. When increasing the speed is not possible because of real-time constraints (e.g. live broadcast of video content) the effect can be adapted to slow playing speed and increase the speed of video playback towards the correct speed as the user becomes more relaxed.

Smear, Delay, Time Diffusion

A blurring effect can be achieved by averaging images in time. Portions of the video images that are stationary between frames will not be affected and therefore remain sharp. However, moving image parts will appear blurry. The amount of blur may be controlled by the adjusting the time period used for averaging the images. The amount of blur can be linked to the degree of relaxation.

Only at the Rims/PiP/Split Screen

A user may prefer to see at least a significant part of a displayed image unaltered. Therefore, a number of options mentioned above may be preferably applied only at the rims of the displayed images/video. Another option is to process only part of the image in a splitscreen mode for example. In this way the user additionally can get feedback on the distance to the desired end state.

Match Audio/Video Effects

A visual effect can be accompanied by a similar effect in the audio. For instance for the 'tunnel' effect the audio could be processed such that it sounds far away at first, but comes closer once the user becomes more relaxed. For the speed variations the pitch of the audio can be varied accordingly.

The invention claimed is:

1. A system for modifying a psychophysiological state of a subject comprising:
   a sensor configured to detect a psychophysiological measure of the subject;
   a processor configured to process the detected psychophysiological measure so as to provide a signal indicative of the psychophysiological state of the subject;

a motive source coupled to the processor and configured to output a haptic stimulus according to a pattern that mimics a desired respiration pattern to gradually guide the subject to a desired psychophysiological state, wherein the desired respiration pattern is a regular or repeated pattern that gradually slows over time; and a television configured to output an output stimulus being at least one or any combination of an audio stimulus and a visual stimulus to the subject, the output stimulus being derived from an audio-visual data signal provided by the television for displaying a content on the television, wherein the processor is further configured to modulate the audio-visual data signal in real time based on the signal indicative of the psychophysiological state of the subject, wherein the television comprises a display arranged in a split-screen configuration comprising plural definable parts, wherein the processor is further configured to display a portion of the content in an unaltered state in a first screen part of the split-screen display, and to display a further portion of the content in an altered state including distortions of characteristics of the content in a second screen part of the split-screen display in response to the modulated audio-visual data signal, and wherein the motive source is further configured to provide feedback to the subject to follow the desired respiration pattern to reduce the distortions of the content displayed in the second screen part as the psychophysiological state of the subject gets closer to the desired psychophysiological state, and wherein the processor gradually restores the content displayed in the second screen part to the unaltered state to match the unaltered state of the content displayed in the first screen part in response to the subject changing the psychophysiological state to the desired psychophysiological state.

2. The system according to claim 1, wherein the output stimulus is configured to provide a signal indicative of a time at which the subject should perform a predetermined physical activity including when to breath in and out.

3. The system according to claim 1, wherein the sensor is further configured to detect a heart beat signal of the subject, and wherein the processor is further configured to determine a regularity of the detected heart beat signal so as to determine a psychophysiological state of the subject.

4. The system according to claim 1, wherein the subject is a first subject, the sensor is a first sensor, the processor is a first processor, and the output stimulus is a first output stimulus, the system further comprising:

a second sensor configured to detect a psychophysiological measure of a second subject;

a second processor configured to process the detected psychophysiological measure of the second subject so as to provide a signal indicative of a psychophysiological state of the second subject; and the television is further configured to output a second output stimulus being at least one or any combination of a second audio stimulus and a second visual stimulus to the second subject, the second output stimulus being derived from a second audio-visual data signal provided by the television, the second processor being further configured to modulate the second audio-visual signal in real time based on the signal indicative of the psychophysiological state of the second subject and a current value of the second audio-visual data signal so as to derive a new value of the second output stimulus.

5. The system according to claim 4, wherein the second output stimulus and the first output stimulus are configured to provide a common output stimulus to the first subject and the second subject, the television being further configured to adjust the common output stimulus in real time based on the signal indicative of a psychophysiological state of the first subject and the signal indicative of the psychophysiological state of the second subject.

6. The system according to claim 5, wherein the first sensor is configured to detect a heart beat signal of the first subject, the second sensor is configured to detect a heart beat signal of the second subject, and wherein the first processor is further configured to determine a regularity of the detected heart beat signal of the first subject and the second processor is further configured to determine a regularity of the detected heart beat signal of the second subject, the common output stimulus being dependent on a difference between the regularity of the detected heart beat signal of the first subject and the regularity of the detected heart beat signal of the second subject.

7. The system of claim 1, wherein the distortions in the content in the second screen part occur only near a periphery of the content displayed on the display, the content extending to the periphery of the second screen part.

8. The system of claim 1, further comprising a lighting system for providing light around the display, wherein the processor is further configured to change the light around the display based on the psychophysiological state of the subject.

9. The system of claim 8, wherein the light varies independent of the content displayed on the display.

10. The system of claim 1, wherein the motive source is housed in a remote control that comprises a memory configured to store data on heart rate variability of the subject, and wherein the processor is further configured to identify the subject based on the stored data and select a preset parameter indicative of the psychophysiological state of the subject.

11. The system of claim 1, wherein the processor is further configured to reward the subject in response to detecting an increased relaxation state of the subject by increasing color vibrancy.

12. The system of claim 1, wherein the processor is further configured to change at least one of a shape and size of the further portion of the content displayed in the altered state on the display based on the psychophysiological state of the subject.

13. The system of claim 1, wherein the processor is further configured to allow the subject to change at least one of a shape and size of the content displayed on the display based on changing the psychophysiological state of the subject.

14. The system of claim 1, wherein the distortions include at least one of magnification of the further portion of the content, slanting the further portion of the content, making the further portion of the content wavy, and display the further portion of the content to appear to be at an end of a tunnel and making the content appear closer to a beginning of the tunnel as the distortions are reduced.

15. The system of claim 1, wherein the processor is configured to process the detected psychophysiological measure by detecting changes in periodicity of a heart beat signal of the subject including:

taking Fourier transforms of portions of the heart beat signal to form transformed signals, taking a logarithm (log) of the transformed signals to form log signals, taking inverse Fourier transforms of the log signals to form final signals,
identifying a peak of the final signal,
determining that the detected physiological psychophysiological measure indicates a low level of relaxation when the peak has a low value indicating a heart of the subject is beating at a heart rate which is not constant, and
determining that the detected psychophysiological measure indicates a high level of relaxation, higher than the low level, when the peak has a high value, higher than the low value, indicating the heart rate is constant.

16. A method for modifying a psychophysiological state of a subject comprising the acts of:
detecting a psychophysiological measure of the subject by a sensor;
processing the detected psychophysiological measure so as to provide a signal indicative of a psychophysiological state of the subject;
outputting an output stimulus being at least one or any combination of an audio stimulus, visual stimulus, haptic stimulus, temperature stimulus and scent stimulus to the subject, the output stimulus being derived from a television signal comprising an audio-visual data signal for displaying television content on a display;
modulating a current value of the audio-visual data signal in real time to form a modulated audio-visual data signal based on the signal indicative of a psychophysiological state of the subject and the current value of the audio-video data signal so as to derive a new value of the output stimulus;
displaying on a first part of the display a portion of the television content in an unaltered state, and displaying on a second part of the display a further portion of the television content in an altered state including distortions of characteristics of the television content in response to the modulated audio-visual data signal;
providing haptic feedback to the subject according to a pattern that mimics a desired respiration pattern to gradually guide the subject to a desired psychophysiological state, wherein the desired respiration pattern is a regular or repeated pattern that gradually slows over time, and to reduce the distortions of the content displayed on the second part of the display as the psychophysiological state of the subject gets closer to the desired psychophysiological state; and
gradually restoring the television content displayed on the second part of the display to the unaltered state to match the unaltered state of the television content displayed on the first part of the display in response to the subject changing the psychophysiological state to the desired psychophysiological state.

17. The method according to claim 16, wherein the output stimulus is configured to provide a signal indicative of a time at which the subject should perform a predetermined physical activity including when to breath in and out.

18. The method of claim 16, wherein the distortions include at least one of magnification of the further portion of the television content, slanting the further portion of the television content, making the further portion of the television content wavy, and display the further portion of the television content to appear to be at an end of a tunnel and making the television content appear closer to a beginning of the tunnel as the distortions are reduced.

19. The method of claim 16, wherein the processing act includes the acts of:
taking Fourier transforms of portions of a heart beat signal to form transformed signals;
taking a logarithm (log) of the transformed signals to form log signals;
taking inverse Fourier transforms of the log signals to form final signals;
identifying a peak of the final signal;
determining that the detected psychophysiological measure indicates a low level of relaxation when the peak has a low value indicating a heart of the subject is beating at a heart rate which is not constant; and
determining that the detected physiological psychophysiological measure indicates a high level of relaxation, higher than the low level, when the peak has a high value, higher than the low value, indicating the heart rate is constant.

20. A non-transitory computer readable medium comprising computer instructions which, when executed by a processor, configure the processor to perform the acts of:
detecting a psychophysiological measure of a subject by a sensor;
processing the detected psychophysiological measure so as to provide a signal indicative of a psychophysiological state of the subject;
outputting an output stimulus being at least one or any combination of an audio stimulus and a visual stimulus to the subject, the output stimulus being derived from a television signal comprising an audio-visual data signal for displaying television content on a display;
modulating a current value of the audio-visual data signal in real time to form a modulated audio-visual data signal based on the signal indicative of the psychophysiological state of the subject and the current value of the audio-video data signal so as to derive a new value of the output stimulus;
displaying on a first part of the display a portion of the television content in an unaltered state, and displaying on a second part of the display a further portion of the television content in an altered state including distortions of characteristics of the television content in response to the modulated audio-visual data signal;
providing haptic feedback to the subject according to a pattern that mimics a desired respiration pattern to gradually guide the subject to a desired psychophysiological state, wherein the desired respiration pattern is a regular or repeated pattern that gradually slows over time, and to reduce the distortions of the television content displayed on the second part of the display as the psychophysiological state of the subject gets closer to the desired psychophysiological state; and
gradually restoring the television content displayed on the second part of the display to the unaltered state to match the unaltered state of the television content displayed on the first part of the display in response to the subject changing the psychophysiological state to the desired psychophysiological state.

21. The non-transitory computer readable medium of claim 20, wherein the processing act includes the acts of:
taking Fourier transforms of portions of a heart beat signal to form transformed signals;
taking a logarithm (log) of the transformed signals to form log signals;
taking inverse Fourier transforms of the log signals to form final signals;
identifying a peak of the final signal;
determining that the detected psychophysiological measure indicates a low level of relaxation when the peak has a low value indicating a heart of the subject is beating at a heart rate which is not constant; and determining that the detected physiological psychophysiological measure indicates a high level of relaxation, higher than the low level, when the peak has a high value, higher than the low value, indicating the heart rate is constant.

22. A television remote control for a television, the remote control being configured to modify a psychophysiological state of a subject and comprising:

a sensor configured to detect a psychophysiological measure of the subject;

a processor configured to process the detected psychophysiological measure so as to provide a signal indicative of the psychophysiological state of the subject; and an output unit coupled to the processor and configured to output an output stimulus comprising a haptic stimulus that comprises a pattern that mimics a gradually decreasing respiration rate to the subject to gradually guide the subject to a desired psychophysiological state, the pattern based on the signal indicative of the psychophysiological state of the subject, the processor further configured to output a television control signal, the television control signal comprising parameters corresponding to the psychophysiological measure, the parameters provided in the television control signal adjust audio and video settings of the television to modulate an audio and video output of the television in real time based on the parameters.

23. The remote control of claim 22, wherein the processor is configured to process the detected psychophysiological measure by detecting changes in periodicity of a heart beat signal of the subject including:

taking Fourier transforms of portions of the heart beat signal to form transformed signals, taking a logarithm (log) of the transformed signals to form log signals, taking inverse Fourier transforms of the log signals to form final signals, identifying a peak of the final signal, determining that the detected psychophysiological measure indicates a low level of relaxation when the peak has a low value indicating a heart of the subject is beating at a heart rate which is not constant, and determining that the detected physiological psychophysiological measure indicates a high level of relaxation, higher than the low level, when the peak has a high value, higher than the low value, indicating the heart rate is constant.

\* \* \* \* \*